US006260415B1

(12) United States Patent
Goebel et al.

(10) Patent No.: US 6,260,415 B1
(45) Date of Patent: Jul. 17, 2001

(54) SYSTEM AND METHOD FOR MATERIAL TESTING, MATERIAL SUITABLE FOR SUCH TESTING AND METHOD FOR PRODUCING SUCH MATERIAL

(75) Inventors: Johann Goebel, Munich; Andreas Mittelbach, Unterhaching, both of (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/247,367

(22) Filed: Feb. 10, 1999

(30) Foreign Application Priority Data

Feb. 12, 1998 (DE) ............................................... 198 05 584

(51) Int. Cl.$^7$ .................................................. G01N 29/00
(52) U.S. Cl. .................................. 73/588; 73/582; 73/801
(58) Field of Search ............................. 73/573, 574, 575, 73/579, 582, 587, 588, 768, 767, 774, 775, 778, 783, 803, 804, 583, 801

(56) References Cited

U.S. PATENT DOCUMENTS

| | | | |
|---|---|---|---|
| 3,504,532 | * 4/1970 | Muenow et al. | 73/579 |
| 3,946,256 | * 3/1976 | Day et al. | 73/587 |
| 4,096,740 | * 6/1978 | Sallee | 73/778 |
| 4,457,174 | * 7/1984 | Bar-Cohen et al. | 73/582 |
| 4,462,257 | * 7/1984 | Gerhart et al. | 73/644 |
| 4,806,292 | * 2/1989 | DeLacy | 73/587 |
| 4,836,030 | * 6/1989 | Martin | 73/800 |
| 4,943,930 | * 7/1990 | Radjy | 73/573 |
| 5,316,857 | 5/1994 | Spiegel . | |
| 5,814,729 | * 9/1998 | Wu et al. | 73/588 |

FOREIGN PATENT DOCUMENTS

| | | |
|---|---|---|
| 4019869 | 1/1992 | (DE) . |
| WO96/07095 | 3/1996 | (WO) . |

* cited by examiner

*Primary Examiner*—Helen Kwok
(74) *Attorney, Agent, or Firm*—W. F. Fasse; W. G. Fasse

(57) ABSTRACT

A material, such as a fiber composite material, has embedded inside at least one, preferably more, surface acoustic wave filters of piezoelectric material for receiving testing energy in a wireless manner and for retransmitting a material quality signal in a wireless manner which is evaluated in a system that has a wireless transmitter for sending testing energy into a material and a wireless receiver for receiving the material quality signal which is then processed and evaluated by a respective processor of the testing system. An output of the processor provides information regarding the nature and quality of the material tested and of the presence and location of any material faults that may be displayed on display screen.

15 Claims, 2 Drawing Sheets

SYSTEM AND METHOD FOR MATERIAL TESTING, MATERIAL SUITABLE FOR SUCH TESTING AND METHOD FOR PRODUCING SUCH MATERIAL

PRIORITY CLAIM

This application is based on and claims the priority under 35 U.S.C. §119 of German Patent Application 198 05 584.6, filed on Feb. 12, 1998, the entire disclosure of which is incorporated herein by reference.

FIELD OF THE INVENTION

The invention relates to a system and a method for material testing. The invention also relates to a material suitable for such testing, particularly fiber composite materials, adhesives, polymer materials, elastomer materials, thermoplastic and thermosetting materials, and to a method for producing such materials.

BACKGROUND INFORMATION

Polymer materials, such as fiber composite materials and structural adhesives, are increasingly used in high stress structures and other structural components due to the stiffness of these materials combined with a relatively low weight or density. However, under high load conditions or under prolonged duration load conditions, such structural components may suffer structural damage within the volume of the material or structural component. Thus, it is a disadvantage of polymer materials that such structural damage generally cannot be ascertained by mere external visual inspection. For example, damages may be caused on an aircraft by impacts with a flying object such as impacts by birds. Such damages are hard to detect or may not be detected at all, whereby high risks are involved.

In order to be able to make quality determinations of such structures and to detect the damage, a multitude of test methods have been developed, including destructive and non-destructive testing methods such as the "woodpecker" method, ultrasound testing, and thermography. Most of these methods are based on an optical or acoustic excitation of the material to be inspected. The resulting stress as a function of time profile is then evaluated to obtain data that permit a person skilled in the art to make conclusions regarding the operational condition of the material tested. However, many of the conventional methods fail where structures are involved having complicated configurations or else an enormous effort and expense is involved in the measuring of the data, for example where it becomes necessary to use temperature controlled testing chambers. Further, the obtained data must be interpreted which requires an exceptionally high degree of experience in order to avoid errors. Another disadvantage of conventional methods is seen in that an evaluation by comparing identical or repeated measuring results is hardly possible because identical coupling conditions which are required for a comparing evaluation are hardly realizable. Another drawback is seen in that in conventional methods only an existing failure can be detected, while an early recognition of possible or impending failures is not possible. Furthermore, many of the known testing methods are not applicable for materials involving adhesive bonding or the adhesive materials themselves, because the required coupling conditions are not realizable with conventional methods.

In a known method for testing materials glass fibers were introduced into the material in order to examine the glass fiber structure by illumination. Such materials require a high effort and expense for their manufacture and for the performance of the testing. Yet, a precise localization of a defect is hardly possible or possible only with great effort and expense.

OBJECTS OF THE INVENTION

In view of the foregoing it is the aim of the invention to achieve the following objects singly or in combination:

to provide a material that by its characteristics is easy to test with a certain recognition of structural defects and to locate the position of a fault or defect within the body of the material or structural component;

to provide a testing method that easily permits an evaluation by comparing test results;

to impart the testability feature into the material at the time of manufacturing the material while still permitting an efficient low-cost manufacturing process;

to provide a testing method that will yield information regarding existing defects and information regarding possible future defects; to provide an apparatus and method for testing different material characteristics, including temperature, modulus of shear, compression, density, and so forth; and to make it possible to perform the transmission of testing signals and reception of test information carrying signals in a wireless manner and without physical contact to provide a non-destructive testing.

SUMMARY OF THE INVENTION

According to one aspect of the invention a material, particularly a fiber composite material, is provided that has integrated or embedded therein, for example embedded therein, one or more sensors functioning as transducers for ascertaining measured values which provide information regarding the status and/or the quality of the material, whereby each sensor is constructed with an antenna for receiving an excitation energy in a wireless manner and for generating a signal which signifies at least one of the material characteristics in response to the received excitation signal wherein the antenna also transmits the material characteristic signals in a wireless manner out of the material.

By integrating or embedding a sensor with an antenna or a plurality of sensors with antennas forming a sensor system into the material, a constantly uniform consistent and optimal coupling of the sensor or sensors to the material is achieved, since the sensor with its antennas or sensors with their antennas become permanent components of the material such as a fiber composite material. Thus, a comparing and evaluation of different testing results obtained at different times from the material and/or from the adhesive bonding in the material becomes possible.

Advantageously the sensors are simultaneously receivers and transmitters for receiving a testing signal and generators for generating and transmitting a material quality signal that signifies at least one or more of the material characteristics in response to a received testing signal that triggers the return transmission of the material quality signal. The received testing signal and the returned material quality signal are both transmitted in a wireless manner. An evaluation and testing unit also operates in a wireless manner for transmitting testing signals and for receiving material quality signals unit. Piezoelectric elements are particularly suited for sensors as used according to the invention. Piezoelectric elements are preferred because they enter into a mutual interaction with the material in which these piezoelectric elements are embedded. Thus, it is possible to introduce the testing energy into the material through the sensors and to retrieve from the material through the sensor the respective material quality signal. For this purpose the sensors are preferably intimately bonded to or into the material. So-called surface acoustic wave (SAW) filters are advantageously used for the present purposes because such filters enter into an intimate contact with the material to be tested which is preferred for the present purposes. A material according to the invention can be tested at any time externally for obtaining a status evaluation without invasion into the material, whereby various material characteristics such as its temperature, its moisture content, its viscosity, its shear modulus compression, and so forth are measurable and the measured results can be evaluated.

In a preferred embodiment, the sensors which act as receiver/transmitters, comprise an antenna structure that is capable of receiving excitation or testing signals and of retransmitting material quality signifying signals that provide the required information to be obtained by the testing. Preferably, the sensors comprise a pick-up structure for a wireless transmission of energy and/or information. The testing energy is transmitted through the present sensors into the material or structural component made of such material and the material quality signifying signals can be interrogated or received in a wireless manner without contacting the material.

The sensors are preferably integrated or embedded in a laminate structure and/or in the area of an adhesive that bonds the laminates to one another. It is preferred that each sensor should have its own encoding so that by way of the material quality signal that is correspondingly encoded by the sensor it is possible to individually identify each sensor and its location within the material or component being tested, for example in a coordinate system so that when evaluating the data a multi-dimensional status image of the structural component or of the entire structure or of the bonding adhesive can be obtained. The image permits then to distinguish between existing defects and potential or beginning defects which then can be localized within the material in accordance with the respective recognition encoding of the particular sensor. It is preferred to uniformly distribute the sensors within the material. However, it is also possible to concentrate the placement of the sensors in areas which are particularly exposed to wear and tear or other dangers, such as impacts.

According to a further aspect of the invention, the present method of manufacturing a material that is testable in accordance with the teachings of the invention, especially fiber composite materials, introduces the sensors into the material, preferably prior to solidification, whereby these sensors have the above described receiver/transmitter characteristics. The transmitter returns a signal that depends on the status and/or quality of the material after it has solidified. Such an introduction of the sensors provides for an efficient and cost effective manufacture of the material or structural component made of such material, whereby the current status can be tested and judged externally at any time so that any defect or any beginning material changes can be localized. As mentioned, it is advantageous to use sensors that are SAW filters which are uniformly and/or randomly distributed in the material, whereby each sensor is preferably provided with its own identification code as mentioned.

The material testing system according to the invention comprises a transmitter for exciting or triggering the sensors with testing energy and a receiver for receiving a material quality signifying signal, as well as a signal processing and evaluating computer circuit. The transmitter preferably or particularly emits sonic waves or electromagnetic waves. The signal processing and evaluating computer circuit preferably has a display for directly displaying defect information and/or information indicating changes in the material tested.

Materials according to the invention are tested by a method according to the invention in which a triggering or excitation energy is transmitted into the material being tested and thus to the sensors, bonded into the material. Preferably acoustic or electromagnetic waves are used as triggering or excitation energy. The reflected signals are received and evaluated for providing the information that signifies the current status and/or quality of the material. As mentioned, the sensors are integrated into the material and the return or reflected signals are generated as a function of the condition or status of the material.

The present method permits a rapid material testing without any substantial effort and expense, whereby the testing is neither invasive nor destructive. Sequentially repeated test results can be compared for an early defect recognition or for determining of structural changes signifying an impending defect because due to the uniform and solid bonding of the sensors to the material a consistent coupling is assured between the sensors and the material. Hence, different test results from tests made at different times are due to changes in the material and not due to inconsistent couplings between material and sensors.

In a preferred testing sequence according to the invention the actual condition as measured through the sensors is compared with a rated condition that is, for example stored in a memory. These rated conditions are preferably ascertained by running a test series immediately upon completion of the manufacturing of the material or structural component. Thus, it is possible to perform a comparing evaluation of the material regarding its current status relative to a starting status, so that material changes can be ascertained. By encoding each sensor correspondingly encoded sensor signals are emitted as material quality signals, whereby it is possible to ascertain the position of the respective sensor within a structural component or in a sheet material. Preferably, the evaluation is accomplished in a matrix or coordinate pattern or by integration over the entire volume of the particular material or structural component. Thus, it is possible to ascertain the current status of the entire structural component or it is possible to localize present defects.

BRIEF DESCRIPTION OF THE DRAWINGS

In order that the invention may be clearly understood, it will now be described in connection with example embodiments, with reference to the accompanying drawings, wherein.

DETAILED DESCRIPTION OF PREFERRED EXAMPLE EMBODIMENTS AND OF THE BEST MODE OF THE INVENTION

Figure 1:
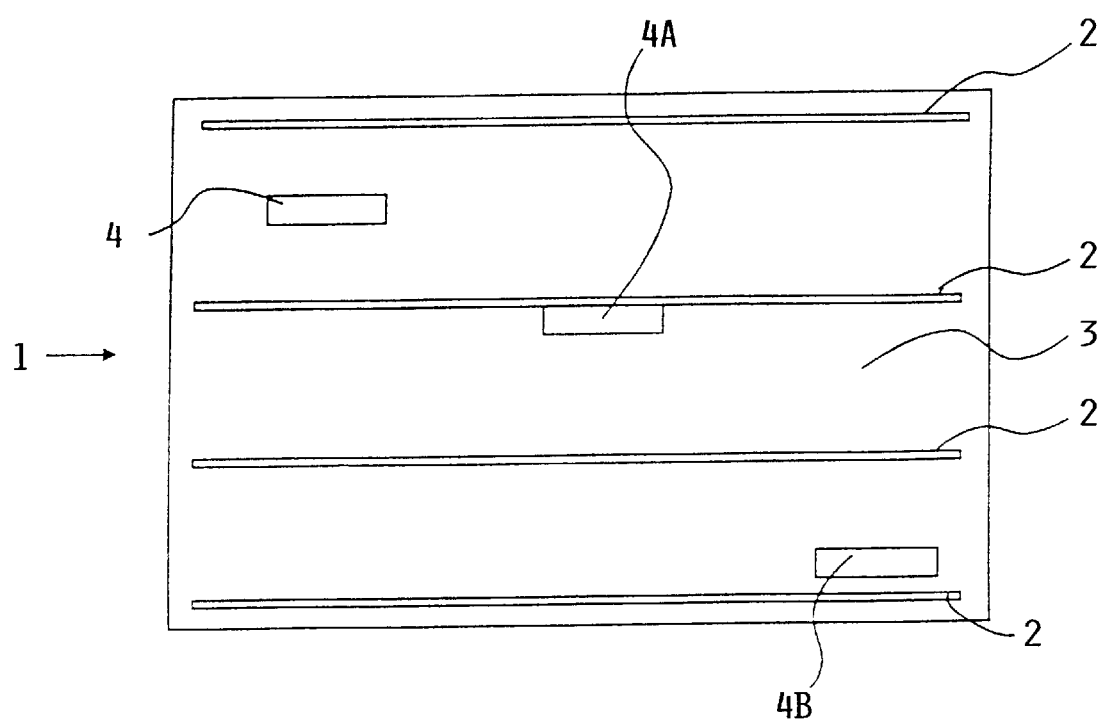
FIG. 1 is a schematic view into the interior of a piece of fiber compound material having, according to the invention, integrated therein sensors for testing purposes.

FIG. 1 shows schematically a view into a material body made of a fiber composite material 1. Fibers 2 are embedded in a matrix material 3 such as a resin or a filler material. Sensors 4 are embedded in the fiber composite material. The sensors 4 are transducers capable of functioning as signal receivers for receiving an excitation or testing signal and as signal transmitters for returning a material quality signal in response to an excitation signal and in accordance with the material qualities. The transmission of testing signals and the return transmission of material quality signals takes place in a wireless manner. Piezoelectric elements are suitable for this purpose. Piezoelectric materials suitable for the purposes of the invention are, for example, lithium niobate (LiNbO$_3$), lithium tantalate (LiTaO$_3$), STX quartz, and piezoelectric polymers. The sensors 4 are embedded so as to be entirely surrounded by and intimately bonded to the matrix material 3. A sensor 4A is embedded so that at least one of its surfaces is in intimate bonded contact with one or more fibers 2. Sensor 4B is embedded close to, but not in contact with a fiber 2. All sensors 4, 4A and 4B are fully enclosed by the matrix material 3.

Several sensor distribution patterns are suitable for the purposes of the invention. Thus, the sensors 4, 4A, 4B may be uniformly distributed throughout the volume of the material or component to be tested. Alternatively, or simultaneously, all or some of the sensors may be randomly distributed in the fiber composite material. The sensors 4 in the form of SAW filters are bonded into adhesive bonding joints between layers of, for example prepregs in order to measure or sense the condition of the bonding quality between neighboring layers in a laminate structure. In all instances the sensors 4 are three-dimensionally distributed throughout the volume of the fiber composite material 1.

Figure 2:
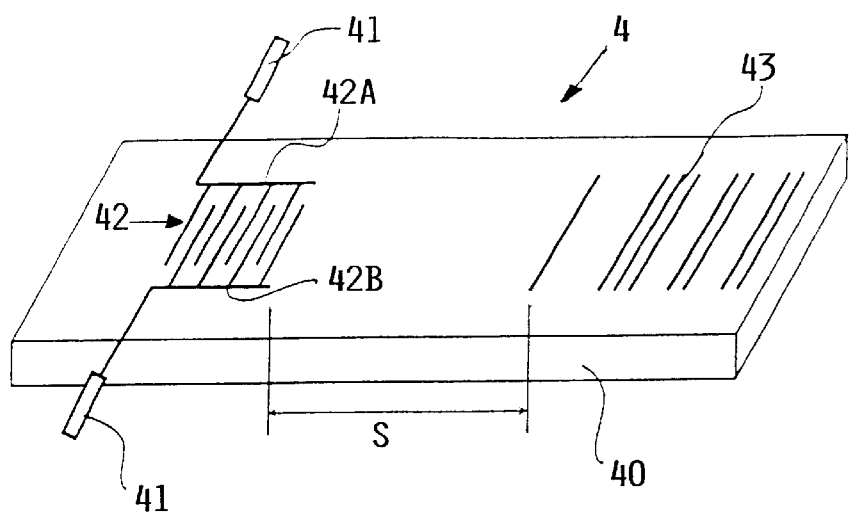
FIG. 2 is a perspective view of a surface acoustic wave filter integrated into a body of material such as fiber composite material.
Figure 3:
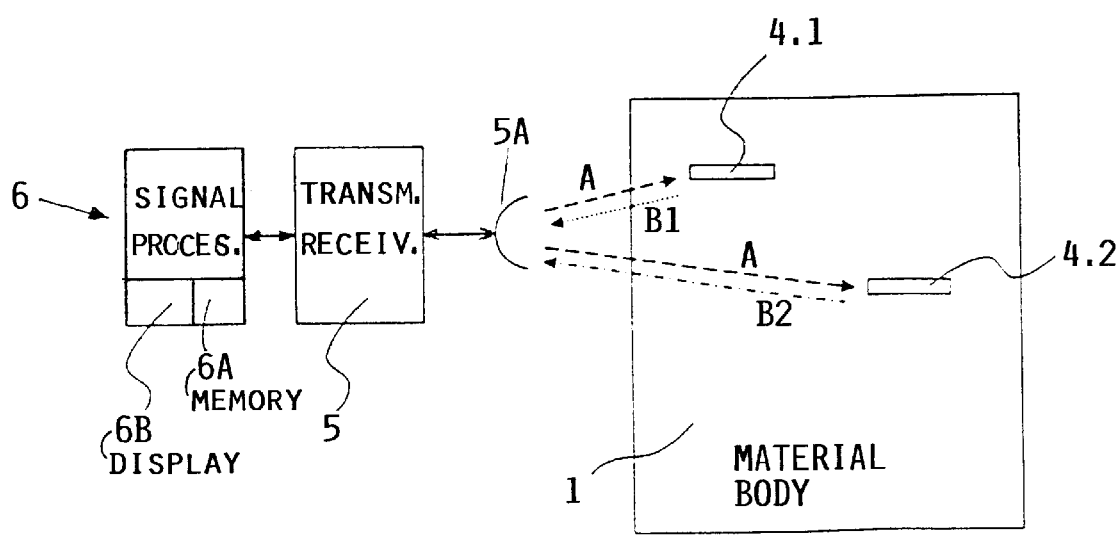
FIG. 3 is a block diagram of a testing system for materials or structural components equipped with sensors according to the invention.

FIG. 2 shows the basic construction of a suitable SAW filter functioning as a sensor 4 in the material 1. An antenna structure 41 is secured to a base plate 40 of piezoelectric material. The antenna structure 41 functions as a receiver as a transmitter antenna. Thus, the sensor can receive testing energy in the form of an electromagnetic wave and a material quality signal containing information regarding the status or quality of the material 1 can be transmitted by the sensor 4 to a transmitter receiver and evaluation unit 6 located outside of the material 1 as shown in FIG. 3. Furthermore, an interdigital structure 42 of conductors is positioned on, e.g. bonded to, the base plate 40 of piezoelectric material. The interdigital conductor structure 42 has a first section 42A and a second section 42B. Each section 42A, 42B has finger-shaped extensions that reach mutually into the spaces between finger-shaped extensions of the respective other section 42A, 42B. These extensions form electrode pairs that cooperate with the piezoelectric base plate 40 for producing electro-acoustic waves or for detecting such waves. For frequency modulation purposes, the interdigital structure 42 can be "chirped" that is, the spaces between neighboring finger-shaped extensions of the sections 42A, 42B are dispersive. In other words, these spacings become smaller away from the antenna structure 41 to generate chirp signals. A chirp signal is a linearly frequency modulated sinus signal of finite duration produced by an SAW filter. The receiver and transmitter antenna structure 41 has a first section connected to the first interdigital electrode section 42A and a second section connected to the second interdigital electrode section 42B, thereby forming a coupling device for introducing testing energy into the material 1 or for transmitting information containing energy from the material 1 to the testing unit 6. A reflector 43 in the form of strip electrodes is secured to the same surface of the piezoelectric base plate 40 as the elements 41, 42. A spacing S is provided between the interdigital structure 42 and the reflector 43. A surface wave produced by the interdigital structure 42 on the surface of the piezoelectric element 40 is reflected by the reflector 43 and returns through the base plate 40 for detection by the interdigital structure 42. The reflector 43 is preferably attached e.g. adhesively bonded to the base plate 40 in a coded form which means that it will generate a response signal that depends on the particular surface acoustic wave filter 4 and thus identifies that filter. The information containing return signal received by the interdigital structure 42 is transmitted through the antenna structure 41 to the outside and thus to the transmitter/receiver and evaluation unit 6 shown in FIG. 3 to be described in more detail below.

The material 1 according to the invention functions for its testing as follows. The sensors 4 integrated into the material 1 are energized or triggered by a material testing signal introduced by a signal generator outside of the material as shown in FIG. 3. In the preferred embodiment an electromagnetic wave is introduced into the material 1, whereby the testing signal is received by the receiver and transmitter antenna 41 secured to the sensor 4. The interdigital structure 42 generates an alternating voltage which in turn produces a surface wave in or on the base plate 40. This surface wave interacts with the material 1, whereby the material characteristics influence the testing signal to generate return signal that bears material quality information. This material quality information includes, for example, the signal propagation velocity through the material over the distance S, the amplitude and phase or frequency of the return signal wave.

The physical material characteristics influence the wave propagation on the surface of the piezoelectric crystal or base plate 40. These characteristics include, for example, the viscosity, the dielectric constant, the temperature, and the density of the material being tested. Structural defects in the material such as fractures, fiber breakage, delamination of a laminated structure, faults in the matrix or resin material, dissolution in the material such as water or vapor or air inclusions or a disillusion of the fiber matrix bonding, especially in the vicinity of a sensor, vary the wave propagation and the variations represent characteristics of the surface waves and thus provide a material quality information because the "quality" of the material is the direct cause of any variations in the signal. Faulty couplings between the sensors and the material being tested are eliminated so that they cannot falsify the test results.

A mechanical surface wave is reflected at the encoded reflector 43, whereby a signal encoding by different spacings between the strip electrodes of the reflector 43 can identify the particular sensor 4. The encoding may be accomplished by the positioning of the individual reflector strip electrodes relative to each other and relative to the above mentioned interdigital positioning of the finger electrode sections 42A, 42B. The encoding may be accomplished by characteristic spacings between neighboring reflector elements 43 or by a characteristic sequence of reflector elements 43 relative to one another. Thus, when the interdigital structure 42 emits a single impulse, a plurality of impulses are reflected and detected at 42, after passing through the spacing S in a direction opposite to the initial travel direction of the testing impulse toward the interdigital structure 42. The detected return impulses provide the material quality signifying signal which is then converted into an alternating voltage. The receiver and transmitter antenna structure 41 emits the material quality signifying signal which includes the encoding for locating the particular sensor 4 within the volume of the material being tested or of a structural component made of such material. The signals are then received by a testing system according to the invention including a transmitter receiver positioned outside the material being tested. The received signals are then processed and evaluated to provide an output signal that yields the required information regarding structural damages or material variations or defects.

The testing wave or energy passing through the material is also influenced by the material characteristics. Thus, the return signal contains information regarding material or structural defects in areas of the material volume not directly next to or close to the sensors 4.

FIG. 3 shows schematically the components of a material testing system according to the invention includes the above-mentioned transmitter/receiver and evaluation unit 6 for testing materials or structural components constructed as taught by the invention. A transmitter/receiver 5 emits an excitation or testing signal A through an antenna 5A into the body of the material 1 to be tested. Signals B1, B2 are returned by the sensors 4.1, 4.2 through their antennas 41 and received through the antenna 5A by the receiver section of the transmitter/receiver 5 for evaluation. The return signals B1, B2 and so forth contain material quality information that signifies material characteristics for the reasons explained above.

For operating the present system the testing energy signal A must be capable of penetrating into the material. Acoustic and/or electromagnetic waves are suitable for this wireless purpose. The energy penetrates into and through the material, is received by the sensors 4 inside the material and a surface wave is generated along the interface between the surface of a sensor 4 and the material 1 as explained above with reference to FIG. 2. The reflectors 43 shown in FIG. 2 reflect an encoded signal back to the sensor 4. The antenna 41 returns the information containing or material quality signal to the antenna 5A of the testing apparatus. The reflected signals are individually encoded differently for each sensor 4. The reflected and encoded surface waves contain the information regarding the status or quality of the material because the physical characteristics of the material being tested influence the amplitude, the phase, and the frequency of the surface wave that forms the material quality return signal. The interdigital structure 42 of each sensor transforms the respective reflected surface wave into an electrical signal. The coupling structure 42, 42A, 42B of each sensor 4 generates a sensor specific electromagnetic signal B1 and B2 as mentioned above. Each of these reflected signals B1, B2 . . . includes the encoding of the respective sensor in addition to the information regarding the material characteristics or material changes or material defects at the location of the respective sensor and its vicinity. The signals B1 and B2 of the individual sensors 4 are then evaluated in the evaluating section 6 connected with its input to an output of the transmitter/receiver 5. The signal evaluation unit 6 is a signal processing computer forming part of the testing system and includes a memory 6A for storing a rated material quality pattern and a display 6B for displaying material quality information.

Different evaluation methods may be employed, for example Fourier analysis, pattern recognition, or by the use of neuron networks. For example, it is possible to cause damage in a test sample or to simulate such damage and to then produce a specific pattern as a reference and further testing is then done relative to such specific reference pattern.

Another method embodiment according to the invention involves establishing for a particular material immediately after its production is completed, a testing pattern that represents the rated condition for that material. The rated condition or pattern is stored in the memory 6A of the signal evaluation unit 6. Any subsequent test results can then be compared as actually measured signals with the rated pattern or condition. If the material has been damaged in the meantime, the actual subsequent test results will yield signals that differ from the signals representing a rated condition. Thus, defects can be detected that are independent of the location of the sensors because the testing wave or energy introduced into the material is influenced by the material characteristics and if faults or defects are present in the material they will influence the actual signal pattern so that it will differ from the rated signal pattern.

The introduction of testing energy into the material 1 can also be accomplished differently. Instead of radiating electromagnetic waves into the material, it is, for example, possible to introduce an acoustic wave into the material by knocking on the material being tested or on the structural component being tested, whereby the sensors 4 detect the respective acoustic wave and material quality signals B1 and B2 and so forth will be returned to the receiver section of the transmitter/receiver 5 through the antenna 5A. In that case, the transmitter is not operated. In this instance the acoustic wave and thus the resulting detected signals are influenced by the characteristics of the material in the vicinity of the sensors 4.

The signal processing and evaluating stage 6 processes and evaluates the returned material quality signifying signals while simultaneously making signal corrections in order to exclude effects which are not caused by material defects or by structural material changes. For example, the signals are processed to make a temperature compensation so that temperature dependent effects on the material are eliminated from the evaluation.

A material 1 according to the invention is manufactured, for example in that one or several sensors 4 are introduced into the material prior to its curing. For example, sensors 4 in the form of SAW filters can be laminated into a fiber composite material or into the adhesive bonding joints between neighboring prepregs prior to curing. With this introduction of the sensors into the material, certain areas or zones of the material 1 can be provided with sensors which have a defined, characteristic encoding for locating the position of structural damages or defects within the volume of the material 1. Further, it is possible to simply disperse SAW filters 4 into the starting materials of which the material is made, whereby a uniform distribution pattern or a random distribution pattern or a statistical distribution pattern of sensors within the volume of the material 1 can be accomplished.

The integration of the sensors 4, especially in the form of SAW filters into the material 1, for example by embedding these sensors, in practicing the invention accomplishes the testing by a wireless transmission of testing signals and of defect information carrying signals regarding the material and the evaluation can be made outside of the material without the need for an operating energy for the sensors. The integrated or embedded sensors 4 guarantee that always the same and optimal coupling is provided between the sensors and the material to be tested. Thus, a comparing evaluation of the test results of the material to be tested or the structure to be tested and any adhesive bonding can be accomplished. The bonding information containing measured value or values can also be picked up outside of the material or structural component so that no invasion or destructive testing is necessary. Furthermore, the present material and system is substantially free of disturbing influences and thus guarantees a reliable operation since the sensors 4 themselves do not comprise any active components and do not require any power supply for their operation.

It is an advantage of the present measuring method that it is possible to sense various values such as temperature, moisture, viscosity, modulus of shear, compression, density and expansion coefficients, and so forth, whereby conclusions may be made with regard to possibly present defects in the material and the location of these defects may be pinpointed. Another advantage is seen in that tests for ascertaining aging defects in the material particularly in polymer materials can be efficiently made. Yet another advantage is the possibility that safety tests, for example on aircraft components, can be made in the shortest possible time, whereby an added benefit is seen in that even beginning structural defects can be recognized in one or more aircraft components without withdrawing the aircraft from service for prolonged periods of time. According to the invention the sensors 4 can be embedded in any of the materials listed above.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A material comprising a material body, at least one surface acoustic wave filter (4) forming a wireless receiver and a wireless transmitter embedded into said material body (1) for testing material characteristics, said at least one surface acoustic wave filter (4) comprising an energy transducer (40, 42) for generating a material quality signal in response to a testing signal received in a wireless manner from outside said material body, said material quality signal signifying at least one of said material characteristics, and wherein said surface acoustic wave filter (4) comprises a receiver/transmitter antenna (41) also embedded in said material body for receiving said testing signal and for transmitting said material quality signal for evaluation outside said material.

2. The material of claim 1, wherein said energy transducer of said at least one surface acoustic wave filter (4) is a piezoelectric element (40).

3. The material of claim 1, wherein said at least one surface acoustic wave filter (4) is solidly bonded to said material body (1) inside said material body (1).

4. The material of claim 1, wherein said material body (1) comprises a laminate structure and wherein said at least one surface acoustic wave filter (4) is embedded in said laminate structure.

5. The material of claim 1, comprising a plurality of surface acoustic wave filters (4) and wherein each of said surface acoustic wave filters comprises means (43) for generating a different encoded identification signal for individually identifying each surface acoustic wave filter.

6. The material of claim 1, comprising a plurality of surface acoustic wave filters distributed in said material body in at least one of the following patterns: a uniform distribution pattern, a random distribution pattern, and a coordinate or matrix distribution pattern.

7. The material of claim 1, wherein said material body (1) is a material selected from the group consisting of fiber composite materials, adhesives, polymer materials, elastomer materials, thermoplastic and thermosetting materials.

8. A method for producing a material having an improved testability, comprising the following steps:

(a) embedding into said material one or more surface acoustic wave filters each forming a wireless receiver and a wireless transmitter, (b) intimately bonding said surface acoustic wave filter or filters to said material inside said material, (c) providing each of said surface acoustic wave filters with a receiver transmitter antenna for wireless receiving of testing energy applied externally of the material and for wireless transmitting of a material characteristic signal to outside of said material, (d) and curing said material with said one or more surface acoustic wave filters and with said receiver transmitter antenna embedded in said material.

9. The method of claim 8, wherein said embedding is performed by distributing a plurality of said surface acoustic wave filters into said material in at least one of the following distribution patterns: a uniform distribution pattern, a random distribution pattern, and a coordinate or matrix distribution pattern.

10. A system for testing a material, said material having at least one surface acoustic wave filter (4) forming a wireless receiver and a wireless transmitter embedded into said material for testing material characteristics, said at least one surface acoustic wave filter (4) comprising an energy transducer (40, 42) for generating a material quality signal in response to a testing signal received in a wireless manner from outside said material, said material quality signal signifying at least one of said material characteristics, and wherein said surface acoustic wave filter (4) comprises a receiver/transmitter antenna (41) also embedded in said material for receiving said testing signal and for transmitting said material quality signal for evaluation outside said material, said system comprising a wireless transmitter (5) outside said material for exciting said at least one surface acoustic wave filter inside said material by wave energy transmitted in a wireless manner through said receiver/transmitter antenna, a receiver outside said material for receiving said material quality signal in a wireless manner, a transmitter/receiver antenna connected to said transmitter and receiver outside said material, and a signal processing and evaluating computer (6) connected to said outside wireless transmitter and receiver for determining said at least one material characteristic of said material characteristics from said material quality signal.

11. A system for wireless testing a material, said system comprising at least one surface acoustic wave filter embedded in said material and functioning as a first wireless receiver and as a first wireless transmitter for receiving testing energy in a wireless manner inside said material and for transmitting a material quality signal in a wireless manner out of said material, said system further comprising a second wireless transmitter (5) for exciting said first wireless receiver by wave energy transmitted in a wireless manner, a second receiver for receiving said material quality signal in a wireless manner, and a signal processing and evaluating computer unit (6) connected to said second receiver for determining at least one material characteristic from said material quality signal.

12. A material testing method comprising the following steps:

(a) introducing into the material to be tested at least one surface acoustic wave filter functioning as a wireless receiver/transmitter;

(b) radiating by wireless transmission into said material, testing energy to be received by said surface acoustic wave filter operating as a receiver in a wireless manner;

(c) transmitting in a wireless manner by said surface acoustic wave filter operating as a transmitter an actual material quality signal representing a status of said material in response to said testing energy received in a wireless manner by said surface acoustic wave filter;

(d) receiving said material quality signal in a wireless manner; and (e) processing and evaluating said material quality signal for providing material quality information.

13. The method of claim 12, further comprising:

(f) storing at least one rated material quality signal in a memory;

(g) comparing said rated material quality signal with said actual material quality signal; and (h) evaluating a result of said comparing to provide said material quality information.

14. The method of claim 13, further comprising:

(i) generating said actual material quality signal as an encoded signal identifying a position of said at least one surface acoustic wave filter in said material to be tested, and (j) determining said position in said evaluating step (h) to locate a material fault.

15. The method of claim 12, further comprising performing said processing and evaluating step (e) with reference to a three-dimensional matrix or three-dimensional coordinate system for ascertaining said actual material quality signal over at least a volume portion of said material or a structural component made of said material or for ascertaining a location of a fault at least within said volume portion.

* * * * *